United States Patent
Tripp et al.

(10) Patent No.: US 6,197,036 B1
(45) Date of Patent: Mar. 6, 2001

(54) PELVIC FLOOR RECONSTRUCTION

(75) Inventors: Hugh Adam Tripp, Mansfield, MA (US); Raymond Rackley, Shaker Heights, OH (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/163,960

(22) Filed: Sep. 30, 1998

Related U.S. Application Data

(60) Provisional application No. 60/060,730, filed on Oct. 1, 1997.

(51) Int. Cl.$^7$ .................................................. A61B 17/56
(52) U.S. Cl. ............................................................ 606/151
(58) Field of Search ................................ 606/151, 213, 606/110, 113, 114, 200, 1, 61, 72; 604/11, 12

(56) References Cited

U.S. PATENT DOCUMENTS

| | | |
|---|---|---|
| 2,671,444 | 3/1954 | Pease, Jr. . |
| 3,054,406 | 9/1962 | Usher . |
| 4,400,833 | 8/1983 | Kurland ........................................ 3/1 |
| 4,452,245 | 6/1984 | Usher . |
| 4,549,545 | 10/1985 | Levy . |
| 4,633,873 | 1/1987 | Dumican et al. . |
| 4,854,316 | 8/1989 | Davis . |
| 4,938,760 | 7/1990 | Burton et al. ............................ 600/29 |
| 4,973,300 | 11/1990 | Wright .................................... 600/37 |
| 4,997,434 | 3/1991 | Seedhom et al. ....................... 606/80 |

(List continued on next page.)

FOREIGN PATENT DOCUMENTS

| | | |
|---|---|---|
| WO 88/01853 | 3/1988 | (WO) . |
| WO 93/10731 | 6/1993 | (WO) . |
| WO 94/19029 | 9/1994 | (WO) . |
| WO 94/28799 | 12/1994 | (WO) . |

OTHER PUBLICATIONS

Petros: The Intravaginal Slingpasty Operation, Minimally Invasive Technique for Cure of Urinary Incontinence in the Female, Augt NZJ. Obstet Gynaecol 4:453–461 (1996).

International Search Report for International Patent Application No.PCT/US98/20439 (corresponding to U.S.S.N 09/163,960), Jan. 15, 1999, 8 pgs.

Bayer: A new approach to primary strengthening of colostomy with Marlex® Mesh to prevent paracolostomy hernia, Surgery, Gynecology and Obstetrics 163: 579–580 (1986).

Cruikshank: Reconstructive procedures for the gynecologic surgeon, Am. J. Obstetrics and Gynecology 168: 469–475 (1993).

Falconer: Clinical Outcome and Changes in Connective Tissue Metabolism After Intravaginal Slingplasty in Stress Incontinent Women, Int. Urogynecol. J. 7: 133–137 (1996).

Kovac: Pubic Bone Suburethral Stabilization Sling for Recurrent Urinary Incontinence, Obstetrics and Gynecology 89:624–627 (1997).

(List continued on next page.)

Primary Examiner—Michael Buiz
Assistant Examiner—Vikki Trinh

(57) ABSTRACT

Herniation, including cystocele, rectocele and enterocystocele may be treated with prefabricated repair patches. The repair patches include a natural or synthetic biocompatible material having a shape adapted to support herniated tissue. The patch also contains a plurality of apertures positioned in the central plane of the patch which may permit ingrowth and may also be an attachment site for pexing sutures. The patch may be covered with coating to decrease the possibility of infection, and/or increase biocompatibility. The coating may also include one or more drugs, for example, an antibiotic, an immunosuppressant, and/or an anticoagulant.

33 Claims, 4 Drawing Sheets

U.S. PATENT DOCUMENTS

| | | | |
|---|---|---|---|
| 5,013,292 | 5/1991 | Lemay | 600/30 |
| 5,026,398 | 6/1991 | May et al. | 623/13 |
| 5,122,155 | 6/1992 | Eberbach | 606/213 |
| 5,147,374 | 9/1992 | Fernandez | 606/151 |
| 5,195,542 | 3/1993 | Gazielly et al. | 128/898 |
| 5,252,701 | 10/1993 | Jarrett et al. | 528/354 |
| 5,254,133 | 10/1993 | Seid | 606/215 |
| 5,258,000 | 11/1993 | Gianturco | 606/151 |
| 5,290,217 | 3/1994 | Campos | 600/37 |
| 5,337,736 | 8/1994 | Reddy | 128/20 |
| 5,362,294 | 11/1994 | Seitzinger | 600/37 |
| 5,366,479 | 11/1994 | McGarry et al. | 606/219 |
| 5,368,602 | 11/1994 | de la Torre | 606/151 |
| 5,425,984 | 6/1995 | Kennedy et al. | 428/229 |
| 5,441,508 | 8/1995 | Gazielly et al. | 606/151 |
| 5,451,235 | 9/1995 | Lock et al. | 606/213 |
| 5,474,543 | 12/1995 | McKay | 604/272 |
| 5,527,341 | 6/1996 | Gogolewski et al. | 606/232 |
| 5,611,515 | 3/1997 | Benderev et al. | |
| 5,634,931 * | 6/1997 | Kugel | 606/151 |
| 5,681,310 | 10/1997 | Yuan et al. | 606/61 |
| 5,707,647 | 1/1998 | Dunn et al. | 424/443 |
| 5,766,221 | 6/1998 | Benderev et al. | 606/232 |

OTHER PUBLICATIONS

Petros: The Intravaginal Slingplasty Operation, a Minimally Invasive Technique for Cure of Urinary Incontinence in the Female, Aust. NZ 1. Obstet. Gynaecol. 36: 453–461 (1996).

Petros: Ambulatory Surgery for urinary incontinence and vaginal prolapse, Med. J. Aust. 161: 171–172 (1994).

Ulmsten: An Ambulatory Surgical Procedure Under Local Anesthesia for Treatment of Female Urinary Incontinence, Int. Urogynecol. J. 7: 81–86 (1996).

Ulmsten: Intravaginal Slingplasty (IVS): An Ambulatory Surgical Procedure for Treatment of Female Urinary Incontinence Scand., J. Urol. Nephrol 29: 75–82, (1995).

Webster: Voiding dysfunction following cystourethropexy: Its evaluation and management, J. Urology 144: 670–673 (1990).

Zimmern: Transvaginal Closure of the Bladder Neck, Seminars in Urology 4: 30–32 (1986).

* cited by examiner

PELVIC FLOOR RECONSTRUCTION

CROSS-REFERENCE TO RELATED APPLICATION

This incorporates by reference and claims priority to and the benefit of U.S. provisional patent application Ser. No. 60/060,730, which was filed on Oct. 1, 1997.

TECHNICAL FIELD

The present invention relates to patches for use in supporting tissues, organs, parts of organs, or other such anatomical structures. The patches may be used in a variety of pelvic floor reconstruction or stabilization procedures, including treatment of cystoceles, rectoceles, enteroceles, or enterocystoceles. More particularly, the present invention relates to prefabricated patches, methods of making the patches, and kits including the patches.

BACKGROUND INFORMATION

Damage to the pelvic floor is a serious medical condition which may occur during delivery or due to injury to the vesicovaginal fascia. Such an injury can result in a herniation of the bladder called a cystocele. Other similar conditions are known as rectoceles, enteroceles and enterocystoceles. A rectocele is a herniation of the rectum. An enterocele is formed when the intestine protrudes through a defect in the rectovaginal or vesicovaginal pouch and an enterocystocele is a double hernia in which both the bladder and the intestine protrude. These herniations are serious medical problems that can severely and negatively impact a patient both physiologically and psychologically.

Treatment of these conditions requires repositioning of the protruding organs or portions thereof. Existing tissue is often compromised facilitating the need to use a synthetic patch. Current medical procedures for repositioning the protruding organs or portions thereof may be time consuming or invasive. Hence, there is a need for reducing the amount of time which these procedures require and the invasiveness of the procedures.

SUMMARY OF THE INVENTION

The present invention relates to prefabricated repair patches, methods of making the patches, kits comprising the patches, and methods of using the patches to treat pelvic floor weakening and herniation, including cystoceles, rectoceles, and enteroceles.

One aspect of the invention features a prefabricated patch used in pelvic floor reconstruction procedures, including treatment of cystoceles, rectoceles, enteroceles and enterocystoceles. The patch is made of a natural or synthetic biocompatible material suitable for implantation into the body and has a plurality of apertures formed in a central portion of the patch.

Embodiments of this aspect of the invention can include the following features. For example, the natural or synthetic biocompatible material may be made of a material which facilitates tissue ingrowth, and it can have a plurality of interstices in which tissue ingrowth may occur. Also, the natural or synthetic biocompatible material may be adapted to be cleanly trimmed with scissors without generating sharp edges or spines. The synthetic biocompatible material can be absorbable, and it can be a woven or knitted material such as Hemashield® (available from Meadox Medical, 112 Bauer Drive, Oakland, N.J. 07436). In yet another embodiment of the patch, the natural or synthetic biocompatible material is coated. In some embodiments, the coating on the biocompatible material is absorbed after implantation to facilitate tissue ingrowth into the natural or synthetic biocompatible material. In another embodiment of the patch, the natural or synthetic biocompatible material is impregnated with an antibiotic. In one embodiment, the patch is impregnated with bacitracin. In another embodiment the patch is impregnated with polymixim. In another embodiment the patch is impregnated with neomycin. In some embodiments, the patch is capable of releasing a drug, and the drug can be released over time.

The plurality of apertures formed in the central portion of the patch provide enhanced vascularity and are adapted to permit rapid tissue ingrowth after the patch is installed. The apertures may also be used for pexing sutures. The apertures may be substantially circular. Preferably, the apertures are positioned on the patch at locations which reduce the likelihood of crumpling. For example, the apertures may be positioned at locations which lie outside of the force lines created when the patch is attached to a supporting anatomical structure or tissue. The apertures may be positioned at locations adapted to equalize the distribution of force on the patch when the patch is attached to a supporting anatomical structure or tissue. In one embodiment the apertures are also adapted for suture attachment or for allowing a suture to pass therethrough. In some embodiments, the material around the periphery of the apertures is reinforced. In other embodiments, the apertures are strengthened with a reinforcing device.

In some embodiments, the corners of the patch are adapted to receive a suture, thus serving as suture attachment sites. In other embodiments, the corners of the patch are adapted to receive more than one suture. In some embodiments, the sutures may be pre-attached to the patch.

In another aspect, the invention relates to a kit for performing a pelvic floor reconstruction or stabilization. The kit comprises a sterile natural or synthetic biocompatible material having a shape adapted for use in the procedures discussed above. The natural or synthetic biocompatible material has a plurality of apertures formed therein.

In one embodiment of the kit, the patch is packaged and both the patch and packaging are sterile. In another embodiment of the kit, the patch is a filamentous material coated with a coating to decrease the possibility of infection and/or increase biocompatibility. The coating can also include collagen or a polymeric material. In some embodiments, the coating may also include one or more drugs, for example and antibiotic, an immunosuppressant, and/or an anticoagulant. The packaging may be ultra-violet proof to protect the coating and/or drug.

Yet another aspect of the invention involves a method of making a patch for use in pelvic floor reconstruction procedures, such as those for treating cystoceles, rectoceles, enteroceles or cystoenteroceles. A natural or synthetic biocompatible material is cut into a shape adapted for pelvic floor stabilization and apertures are formed in the natural or synthetic biocompatible material. The material is typically sterilized, and a coating and/or drug can be applied to the material. The material can then be packaged.

In still another aspect, the invention features a method of stabilizing the pelvic floor. A patch is provided and it comprises a natural or synthetic biocompatible material having a shape adapted for pelvic floor reconstruction and a plurality of apertures formed in a central portion of the patch. One side of the patch is placed in contact with the tissue to be supported. The patch is secured to a supporting structure such as tissue, fascia, ligament, bone, muscle or other such anatomical structures having sufficient strength to allow the patch to be secured thereto without tearing the supporting structure. The supporting structure is located such that when the patch is secured thereto the herniated tissue is re-positioned in a location which alleviates the hernia. The force applied is sufficient to reposition the tissue in normal anatomical position. One embodiment of this method, the patch is secured by a at least one suture which is connected to a bone anchor which is attached to bone. In another embodiment, at least one suture can be attached to anatomical structures other than bone such as the arcus tendinous fascia pelvis, the ileal pectineal, or the pubococcygeous muscle complex.

In one embodiment, the method is a treatment for a cystocele and the tissue to be supported is the bladder or a portion thereof. The patch is placed in contact with the tissue beneath the bladder or portion thereof. The patch is connected to the supporting structure such that a biasing force is applied to the bladder or portion thereof to reposition the bladder or portion thereof such that the cystocele is alleviated. In further embodiments, the supporting structure may be the pubic bone, a ligament, or muscle tissue. The patch may be connected to the supporting structure through a suture or other fastener. In one embodiment, the suture or other fastener is secured to the supporting structure with a securing device such as a bone anchor. In one embodiment of the method, the tissue to be supported further comprises the bladderneck and at least a portion of the patch contacts the bladderneck to provide a biasing force to the bladderneck which repositions the bladderneck. The patch can be trapezoidal in shape and the narrower end of the trapezoid contacts the bladderneck while the wider end of the trapezoid contacts the bladder. In another embodiment of the method, the anchor is positioned in a pubic bone. In yet another embodiment of the method, at least one suture may be attached to the patch at each of the corners. In one embodiment, the method further comprises introducing the patch percutaneously. In another embodiment of the method, the patch is introduced without invasive surgery.

In a further embodiment, the method is a method of treating a rectocele and the tissue to be supported comprises the rectum or a portion thereof. In such procedures, the patch is placed in contact with the rectum or a portion thereof or the tissue adjacent to the rectum or a portion thereof to reposition the rectum or a portion thereof.

In a further embodiment, the method is a method of treating an enterocele and the tissue to be repositioned comprises the intestine or a portion thereof. In such procedures, the patch is placed in contact with the intestine or a portion thereof or the tissue adjacent to the intestine or a portion thereof to reposition the intestine or a portion thereof.

In a further embodiment, the method is a method of treating an enterocystocele, and the tissue to be supported comprises the bladder and the intestine or portions thereof. In such procedures, the patch is placed in contact with the bladder and intestine or portions thereof or the tissue adjacent to the bladder and intestine or a portions thereof to reposition the bladder and intestine or a portions thereof.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
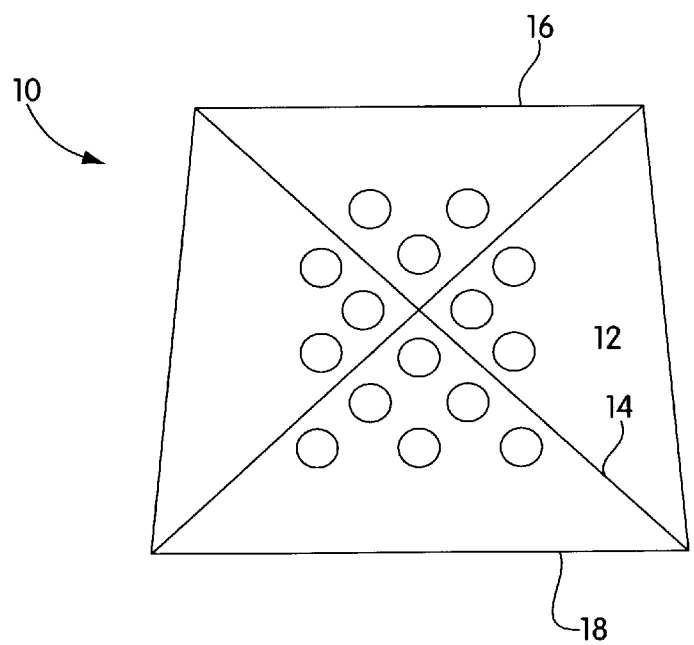
FIG. 1 is a plan view of a preferred embodiment of the patch of the present invention.

The present invention relates to prefabricated patches for use in pelvic floor reconstruction. More particularly, the patches are useful in pelvic floor reconstruction procedures, such as procedures for treating cystoceles, rectoceles, enteroceles, and cystoenteroceles.

The present patches are designed to be implanted in a patient in whom a hernia has resulted in an organ or portion of an organ protruding from its normal position. For example, the patient may have a cystocele whereby the hernia causes the bladder to protrude from its normal position. Alternatively, the patient may have a rectocele whereby the hernia causes the rectum to protrude from its normal position. The patient may also suffer from an enterocele in which the hernia causes the intestine to protrude from its normal position. In addition, the patient may have a cystoenterocele in which the hernia causes both the bladder and the intestine to protrude from their normal positions.

In each of the above conditions, the protruding organ or portion thereof may be restored to its normal position using the present devices and methods. In such procedures, one side of the patch is placed in contact with the organ or portion thereof which is to be repositioned or the tissue adjacent to the organ or portion thereof which is to be repositioned. The patch is secured to a support structure through a fastener such as a suture. The support structure may be any structure having sufficient strength to allow the support to be secured thereto without tearing the support structure. For example, the support structure may be bone, fascia, ligament or muscle. The support structure is positioned such that when the patch is secured thereto, the patch will apply a biasing force to the tissue to be repositioned such that the tissue to be repositioned is restored to its normal position.

The patches of the present invention comprise a natural or synthetic biocompatible material having a plurality of apertures therein. The biocompatible material may be any of a variety of materials. In some embodiments the patch may be made of a material which facilitates tissue ingrowth. For example, the patch may be made of a material having a plurality of interstices, openings or pores therein which permit tissue ingrowth.

The patch may be fabricated from any of a variety biocompatible materials. Such materials may be naturally occurring or synthetic, non-filamentous or filamentous, elastic or inelastic, and may be porous, microporous, perforated, or impermeable. The properties of the patch may be selected as appropriate based on the surgical procedure used to implant the patch and the application for which the patch is used.

Synthetic polymeric materials including, polyester such as Hemashield®, polytetrafluoroethylene (PTFE) such as GoreTex®, polyethylene terephthalate (PET), fluorinated ethylene propylene resin (FEP), polyurethane, or nylon can also be used to form the patches. The synthetic polymeric material can be woven, knitted, or nonknitted. In one embodiment, filaments made from synthetic materials may be braided together to form strands or threads which can be woven, braided, or knitted together to form strips of fabric. Preferably, the synthetic filamentous material is polyester. In one embodiment of the patch, the biocompatible material may be adapted to be cleanly trimmed with scissors without generating sharp edges or spines.

In a preferred embodiment the patch may be made of knitted collagen coated polyester such as Hemashield® (available from Meadox Medical, 112 Bauer Drive, Oakland, N.J. 07436).

The patch can be made from natural materials using autologous, allogenic, or xenogenic material. The natural material can be fibrous tissue, fascia including the fascia lata and rectus fascia, dura, pericardium, striated muscle or part of the vaginal wall. Tissue from xenogenic or allogenic sources may be freeze dried to reduce the immune response to the implanted patch. Patches made from natural material include a plurality of apertures formed in the center portion and can be a shape adapted to support herniated tissue and/or the bladderneck.

Additionally, the patch material may be impregnated with antibiotics or other agents which can be delivered from the surface of the patch as well as through the pores, micropores or perforations. Impregnation with antibiotics or other agents may be facilitated by coating the patch with collagen.

A coating may also be applied to the patch. The coating may be applied to the surface of the material or may be impregnated within the material. The coating may be used to deliver a number of compounds, such as antibiotics, anti-coagulant agents, e.g., heparin, immunosuppressant agents and/or other drugs. In some embodiments, the drug may be released over time. The coating also blocks the interstices of the underlying patch material, thereby decreasing the risk of infection by sequestering the interstices of the patch from contact with microorganisms encountered during implantation of the patch. Preferably, the coating is absorbed after implantation to facilitate tissue ingrowth into the interstices, pores, micropores and/or perforations of the patch material.

Suitable coatings include polyglycolic acid, polylactic acid, blends of polyglycolic acid and polylactic acid, gelatin, polyvinyl alcohol, and polyvinyl pyrrolidone. A preferred coating is a smooth layer of collagen, such as that provided on the Hemashield® available from Meadox. (Meadox Medical, 112 Bauer Drive, Oakland, N.J. 07436 or Boston Scientific Corporation, One Boston Scientific Place, Natick, Mass. 01760.) The smooth collagen coating protects the interstices of the underlying patch material from bacterial contact during implantation, thereby decreasing the risk of infection as previously discussed. The collagen coating can also enhance tissue compatibility. Additionally, the collagen coating can facilitate the uptake of antibiotics to reduce the risk of infection. After placement in the body, the collagen is gradually absorbed, facilitating tissue ingrowth into the underlying filamentous material.

The patches of the present invention can also be made of absorbable materials. Such absorbable patches preferably remain structurally intact for at least three months while supporting tissue ingrowth. Thereafter, the patches may be fully absorbed. Preferably, the patches are fully absorbed over a period of months following the three month period in which the patch is intact. Preferably, the absorbable patch is made of polylactic acid or polylactic acid/polyglycolic acid copolymers.

The patch may have a variety of shapes adapted for use in pelvic floor reconstruction procedures. For example, the patch may be trapezoidal, square, rectangular, oblong, ovoid, or may be an elongated incurvate shape. Those skilled in the art will appreciate that the patch may have a variety of other shapes depending on the procedure in which it is being used and the materials of which it is made.

The patch has a plurality of apertures therein which provide enhanced vascularity and are adapted to permit rapid tissue ingrowth after the patch is installed. The apertures may also be used for pexing sutures. Preferably, the apertures are positioned on the patch at locations which reduce the likelihood of crumpling. For example, the apertures may be positioned at locations which lie outside of the force lines created when patch is attached to a supporting anatomical structure or tissue. The apertures may be positioned at locations adapted to equalize the distribution of force on the patch when the patch is attached to a supporting anatomical structure or tissue. In one embodiment the apertures are also adapted for suture attachment or for allowing a suture to pass therethrough. In some embodiments, the material around the periphery of the apertures is reinforced as described in U.S. patent application entitled, "Stabilization Sling for Use in Minimally Invasive Pelvic Surgery," Ser. No. 09/023,398, filed Feb. 13, 1997, which is hereby incorporated by reference. In embodiments using synthetic material, the material around the periphery of the aperture can be reinforced by heat sealing or ultrasonic sealing the material. The apertures can also be strengthened with a reinforcing device as described in U.S. patent application entitled, "Stabilization Sling for Use in Minimally Invasive Pelvic Surgery," Ser. No. 09/023,398, filed Feb. 13, 1997, which is hereby incorporated by reference. For example, reinforcing devices can be inserted into the material. The reinforcing device can define the periphery of the aperture and strengthen the patch in the area of the apertures. In a preferred embodiment, the one piece reinforcing device can be made from biocompatible plastics or metals, such as stainless steel or titanium. Alternatively, a multiple piece interlocking reinforcement device can be inserted into the material.

In some embodiments, the corners of the patch are adapted to receive a suture, thus serving as suture attachment sites. In other embodiments, the corners of the patch are adapted to receive more than one suture. In some embodiments, the sutures may be pre-attached to the patch.

Referring to FIG. 1, there is disclosed a plan view of a preferred embodiment of the patch 10 of the present invention. The patch of FIG. 1 has been cut into a generally elongate trapezoid shape adapted for pelvic floor reconstruction, with a central plane extending between a more narrow first end 16 and a wider second end 18. Introduced into the natural or synthetic biocompatible material are a plurality of tissue ingrowth apertures 12. Tissue ingrowth apertures are prefabricated in the central plane of the patch 10. The cross lines 14 represent force lines along which tension is transmitted when the patch is attached to the supporting structure at the corners. In a preferred embodiment, the apertures are positioned so that they lie outside of the force lines.

Figure 2:
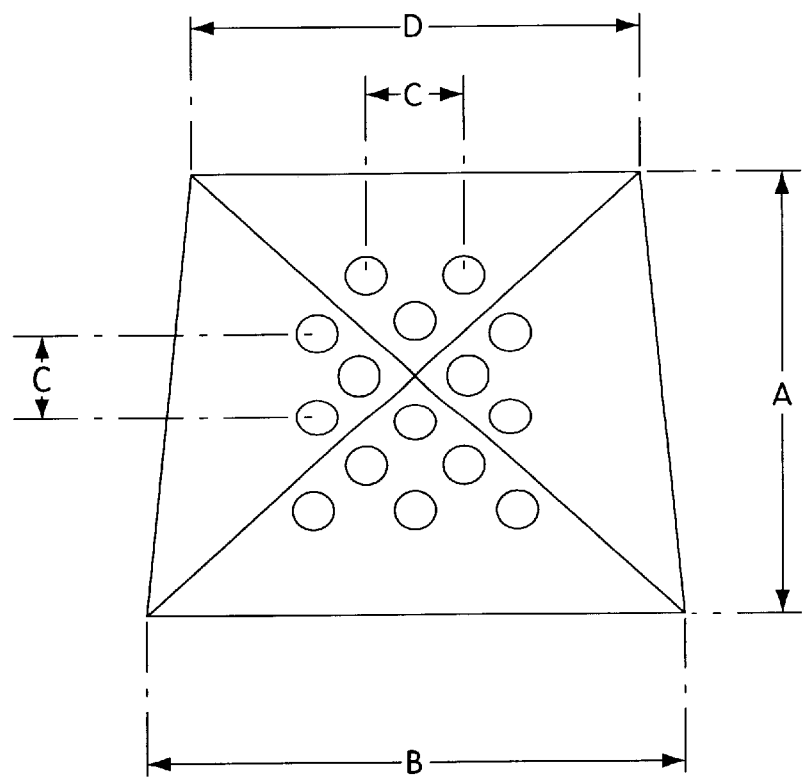
FIG. 2 is a plan view of a preferred embodiment of the patch of the present invention showing preferred dimensions.

The dimensions of a preferred embodiment are shown in FIG. 2. The approximate dimensions, in inches, are as follows: A=1.97; B=2.17; C=0.4; and D=1.78. Preferably, the diameter of the apertures is 0.17 inches. However, those skilled in the art will appreciate that the dimensions of the patch may vary depending on the procedures in which it is used and anatomical variations.

The present patches may be cut into the desired shape prior to providing them to the physicians. This eliminates the need for the physician to cut the patch material into the desired shape during the surgical procedure, thereby reducing the time of the procedure as well as the complexity of the procedure. In addition, providing the patches in precut form may reduce the amount of tissue dissection required for the implantation procedure because the chance that the physician will cut the patch into a size or shape which does not minimize the amount of tissue dissection is eliminated. The patches of the present invention may be individually packaged and/or sterilized prior to purchase. The packaging may protect the patch during storage. For example, in embodiments in which the patch material comprises a collagen coated filamentous material, the packaging may protect the patch from damage by ultraviolet light. The patch may be soaked in an antibiotic solution, such as a solution of neomycin, bacitracin, or polymixim, to prevent microorganisms from collecting on and colonizing the surface of the patch during manipulation, thereby reducing the risk of infection following implantation of the patch. The patch may also be sterilized by ethylene oxide or irradiation. Uptake and delivery of the antibiotic may be enhanced by using a coated patch as described above. In additional embodiments, the patch may be provided to the physician with the sutures pre-attached.

Use of the patch to treat a condition in which an organ or portion thereof protrudes from its normal position will now be described using treatment of a cystocele as an example. If desired, the bladderneck may be stabilized in addition to repositioning the bladder.

A minimally invasive percutaneous method of patch delivery and stabilization to treat an incontinent patient will now be described with reference to FIGS. 3–6. Preoperatively, the patient receives broad spectrum antibiotics, such as gentamicin and ampicillin. The patient is placed in the dorsal lithotomy position and regional or general anesthesia is administered. Preparation of the patient emphasizes isolation of the anus with a stapled towel or plastic drape. A Foley catheter is placed.

Figure 3:
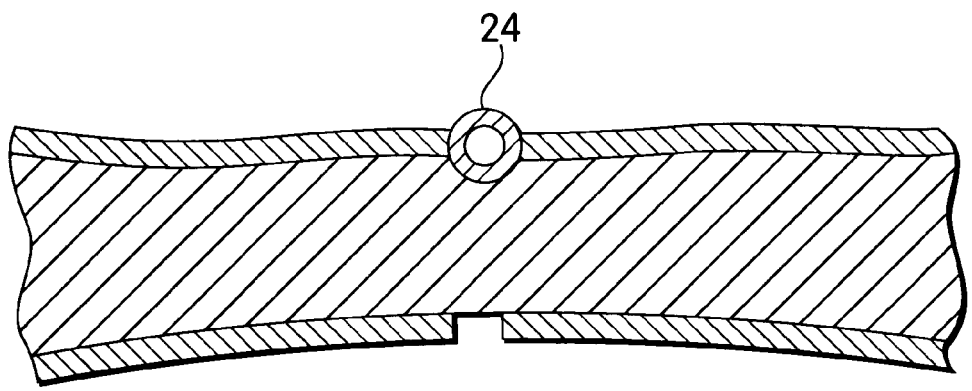
FIG. 3 is a schematic cross-sectional view taken through the urethra and upper vaginal wall illustrating an incision in the upper vaginal wall.
Figure 4:
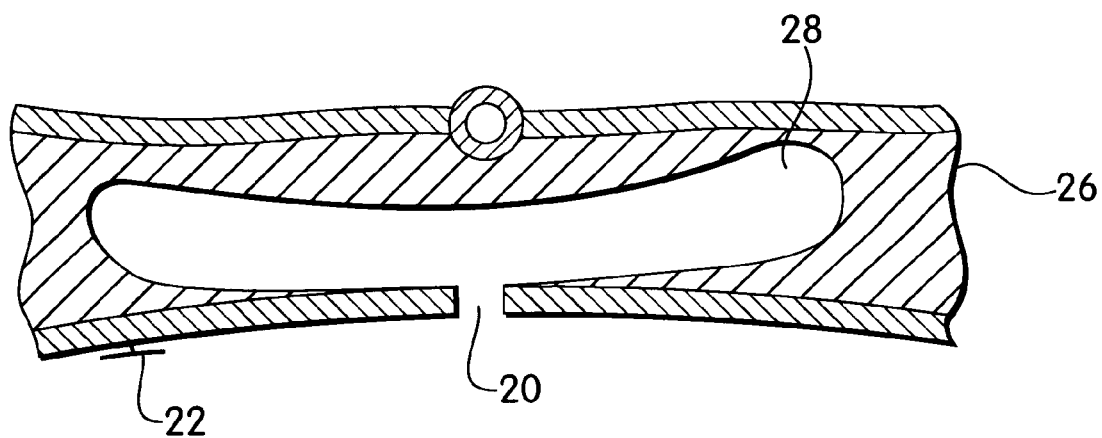
FIG. 4 is a schematic cross-sectional view taken through the urethra and upper vaginal wall illustrating a bilaterally extending pocket created by blunt dissection.

A midline incision 20 is made in the upper vaginal wall 22 beneath the bladderneck, such as at the urethro-vesical junction as illustrated in FIG. 3. The surgeon then inserts an instrument such as surgical scissors through the incision in the upper vaginal wall and bluntly dissects the tissue 26 on both sides of the urethra to create a bilaterally extending pocket which is illustrated in FIG. 4.

The bilaterally extending pocket can also be created and the patch can be inserted using a variety of other minimally invasive instruments/methods including the transvaginal, hiatal and percutaneous approaches disclosed in the U.S. patent application entitled "Transvaginal Anchor Implantation Device," Ser. No. 08/744,439 filed Nov. 8, 1996, the U.S. patent application entitled "Percutaneous and Hiatal Devices and Methods for Use in Minimally Invasive Pelvic Surgery" Ser. No. 09/023,965 filed Feb. 13, 1997, and the U.S. patent application entitled "Method and Apparatus for Minimally Invasive Pelvic Surgery" Ser. No. 09/023,533, filed Feb. 13, 1997, which are hereby incorporated herein by reference.

Either before or after creating the pocket 28, a bone anchor 30, such as a screw in anchor, a press in anchor, or a punch in anchor, is introduced into the pubic bone 34 for fixation of suspensory sutures, with or without predrilling a hole in the pubic bone. For instance, the bone anchor is introduced using a bone anchor implantation device of a type such as that illustrated in FIGS. 15–19 of U.S. Pat. No. 5,766,211, entitled "Bone Anchor Implantation Device", filed Feb. 9, 1995, which is hereby incorporated herein by reference. Bone anchor sites are located by placing the bone anchor implantation device on the body over the area of the pubic bone after visualization or digital palpation over the bone. The surgeon then extends the bone probes distally until both probes have made contact with the pubic bone. Preferably, one anchor 30 for each side (two per patient) is implanted into the tubercle portions of the pubic bone. Preferably, the eyelet of the anchor is recessed below the surface of the bone or flush with the surface of the bone. The anchor 30 preferably has a suture 32 slidably secured thereto prior to implantation of the anchor into the pubic bone so that a first suture end and a second suture end extend from the implanted anchor after removal of the anchor driver.

Two separated approximately one inch transverse incisions are made over the pubic bone as illustrated in the U.S. Pat. No. 5,611,515 entitled "Bladderneck Suspension Procedure", which is hereby incorporated herein by reference, and dissection is carried down to the area of the rectus fascia. The first end of the anchored suture is manually placed into a suture channel of a suture passer of a type such as that illustrated in FIGS. 45 and 45a of the above incorporated U.S. Pat. No. 5,611,515 entitled "Bladderneck Suspension Procedure." The probe is moved distally to lock the suture therein.

Beginning on the right side, the suprapubic wound is stretched cephalad to allow the vertical passage of the suture passer through the rectus fascia with the probe tip fully exposed. Distal advancement of the suture passer is accomplished with the tip proximally retracted within the probe guide. The suture passer is acutely angled into the abdomen so that the point rests on the underside of the pubic periosteum.

While maintaining contact with the underside of the pubis, the suture passer with the probe tip retracted is thereafter passed distally toward the introitus. At the completion of this distal passage, the suture passer can be palpated through the introitus to the right of the urethra 24. The distal end tip of the suture passer is withdrawn from the surface of the pubourethral ligament and gently swept along the pubocervical fascia to the area of the bladderneck under the guidance of a finger within the vagina. Palpation through the vagina may be safely performed to assist in localization of the suture passer tip.

The probe tip is then distally extended. The suture passer is then passed through the endopelvic fascia and into the pocket 28 between the urethra 24 and the upper vaginal wall 22 at which time the probe tip is retracted. The surgeon then guides the suture passer distally into the vagina through the midline incision 20 in the upper vaginal wall 22. The probe is then retracted maximally to the unlocked position to allow the first end of the suture to be manually removed from the suture channel.

The surgeon selects a patch 10, such as patch of the present invention. The surgeon then attaches the sutures 32 to the patch. This step is unnecessary in embodiments were a suture is pre-attached to the repair patch of the invention. If desired, the suture may also be passed through one or more apertures in the patch.

After securing the sutures to the patch, the first end of the suture is placed into the unlocked suture channel and locked into place. The suture passer and suture locked therein are then pulled up through the suprapubic wound. The first end of the suture is then released from the suture channel by manually retracting the probe.

The identical procedure is performed on the left side.

The surgeon places the patch 10 into the pocket 28 through the midline incision 20 in the upper vaginal wall 22. At least a portion of the patch is placed under the cystocele. Where it is desired to stabilize the bladderneck as well as to reposition the bladder, at least a portion of the patch is placed beneath the bladderneck.

As will be apparent to one of skill in the art, the patch may be placed beneath the bladderneck in a variety of ways other than via the pocket 28.

After placing the patch in the pocket or opening, the surgeon aligns the patch. The sutures cause the patch to provide a biasing force on the bladder sufficient to support the bladder in a location which alleviates the cystocele. In addition, if a portion of the patch is under the bladderneck, the patch realigns the bladderneck and the urethra to the correct anatomical position. As will be apparent to one of skill in the art, alignment of the patch relative to the bladderneck and the bladder can be accomplished in a variety of ways, such as by direct visualization.

If the patch is trapezoidal in shape and if it is desired to stabilize the bladderneck as well as to reposition the bladder, the narrower end of the trapezoid is preferably positioned beneath the bladderneck and the wider end is preferably positioned beneath the bladder.

Figure 5:
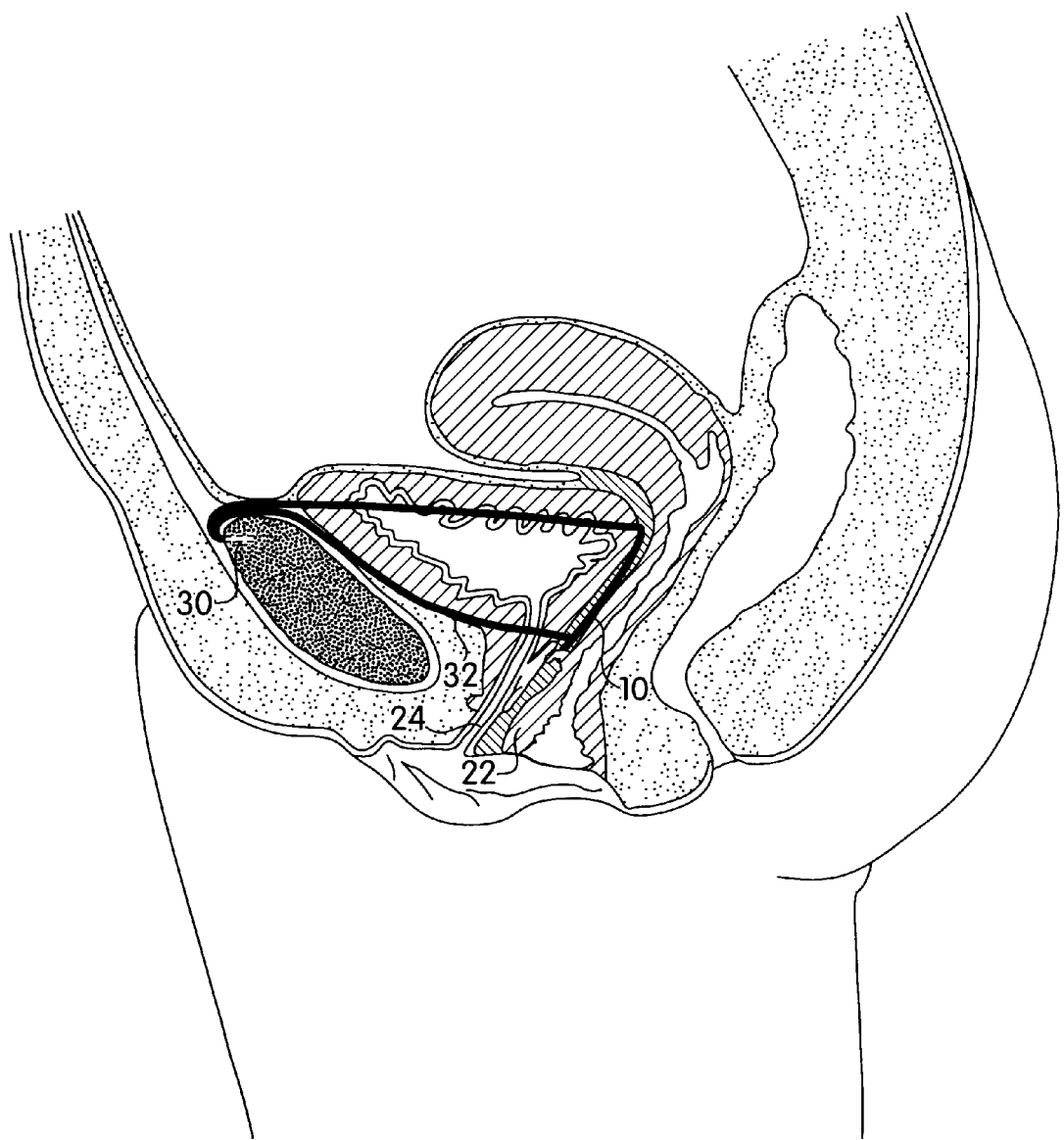
FIG. 5 is a sagittal section of a female pelvis illustrating the location of the patch relative to the bladderneck and the bladder in a procedure in which both the bladderneck and the bladder are repositioned.

After the patch is correctly positioned, the sutures on each side are tied with sufficient tension to reposition the bladder, and, if desired, to support the bladderneck as illustrated in FIG. 5. The Foley catheter is removed prior to tying the suspensory sutures.

Figure 6:
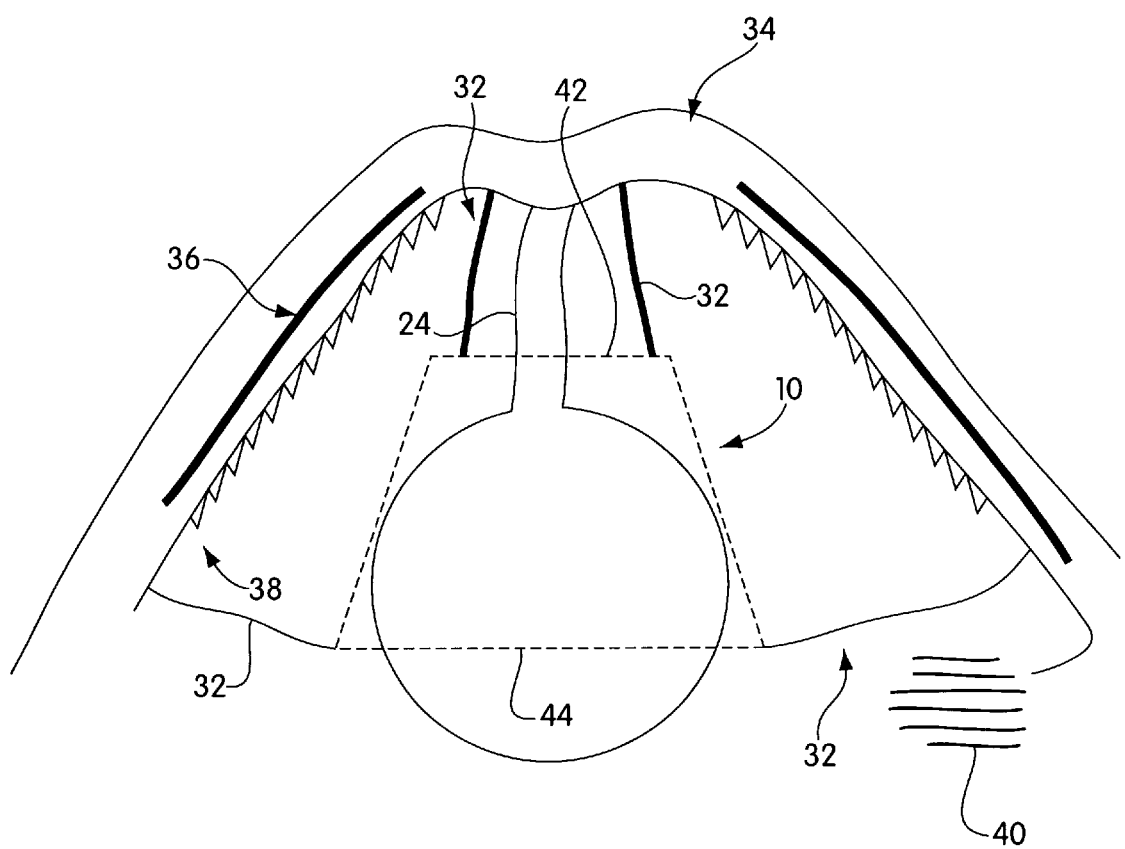
FIG. 6 is a cross section of a female pelvis illustrating the location of the patch relative to the bladderneck and the bladder in a procedure in which both the bladderneck and the bladder are repositioned.

Referring to FIG. 6, in one embodiment, the one or more of the sutures 32 can be laterally attached to anatomical support structures other than the pubic bone, for example, the ileal pectineal (termed Cooper's ligament) 36, the arcus tendinous 38, or the pubococcygenous muscle complex 40. In FIG. 6, the smaller side of the patch 42 is attached to the pubic bone 34 and the larger side 44 is attached to the arcus tendinous fascia pelvis (termed the White Line).

In order to minimize postoperative urinary blockage caused by excessive tension, suture tension is regulated by tying the first and second ends of the sutures across a suture tensioner of a type such as that illustrated in FIGS. 46–49 of the above incorporated U.S. Pat. No. 5,611,515 entitled "Bladderneck Suspension Procedure", filed Apr. 5, 1993. The suture tensioner is thereafter removed and the position of the patch is reconfirmed prior to closing the vaginal and suprapubic wounds.

The wounds are irrigated with an antibiotic solution, such as a bacitracin solution. The wound edges and the rectus fascia at the suture entry points are infiltrated with bupivacaine. A Foley catheter is introduced. Alternatively, a suprapubic tube can be placed, especially in those patients having dexterity problems or an aversion to learning intermittent catheterization.

Following surgery, the patient is given either ciprofloxacin or ofloxacin for ten days. For those patients having a Foley catheter, the catheter is removed approximately one week following surgery. The patient performs intermittent catheterization as necessary until the post-void residuals are less than 75 cc on two consecutive catheterizations. In patients having a suprapubic tube, the suprapubic tube is removed when the postvoid residuals are less than 75 cc following two consecutive urinations.

While the foregoing procedure was described using two bone anchors per patient, one of ordinary skill in the art will recognize that the procedure could also be accomplished using either one anchor per patient, greater than two anchors per patient, other types of surgical fasteners or no surgical fasteners at all.

The patch invention disclosed here is designed to be attachable to any suitable support structure. Examples of such structures include but are not limited to the ligaments, fascia and appropriate muscle structures proximate to the site of attachment. For example, the sutures may be attached to the Cooper's ligament or the rectus fascia without using bone anchors.

All references cited herein are incorporated herein by reference in their entirety.

Although this invention has been described in terms of certain preferred embodiments, other embodiments, which will be apparent to those of ordinary skill in the art in view of the disclosure herein are also within the scope of this invention.

What is claimed is:

1. A surgical patch comprising a piece of biocompatible material including a plurality of apertures and four corners, each corner being adapted to be attached to an anatomical structure by a surgical fastener, thereby forming a first force line extending from one of the corners to a diagonally opposite one of the corners and a second force line extending from a different one of the corners to diagonally opposite one of the corners, wherein none of the plurality of apertures intersects the first force line or the second force line.

2. The surgical patch of claim 1 wherein at least one of the plurality of apertures comprises a substantially circular hole in the piece of material.

3. The surgical patch of claim of 1 wherein the piece of material is capable of being trimmed with scissors.

4. The surgical patch of claim 1 wherein the biocompatible material includes a plurality of interstices.

5. The surgical patch of claim 1 wherein the apertures permit tissue ingrowth after the patch is installed in a body.

6. The surgical patch of claim 1 wherein the apertures are reinforced.

7. The surgical patch of claim 1 wherein the sides form a trapezoidal shape.

8. The surgical patch of claim 1 wherein the apertures are located in the central portion of the piece of material away from the sides.

9. The surgical patch of claim 1 wherein the piece of material comprises a knitted material.

10. The surgical patch of claim 9 wherein the knitted material comprises a polymer.

11. The surgical patch of claim 1 wherein the patch is capable of releasing a drug.

12. The surgical patch of claim 1 wherein the piece of material includes a coating.

13. The surgical patch of claim 12 wherein the coating includes heparin.

14. The surgical patch of claim 12 wherein the coating includes an antibiotic.

15. The surgical patch of claim 12 wherein the coating comprises collagen.

16. The surgical patch of claim 12 wherein the coating comprises polyglycolic acid.

17. The surgical patch of claim 12 wherein the coating comprises polyactic acid.

18. The surgical patch of claim 12 wherein the coating comprises gelatin.

19. The surgical patch of claim 12 wherein the coating comprises polyvinyl alcohol.

20. The surgical patch of claim 12 wherein the coating comprises polyvinyl pyrrolidone.

21. The surgical patch of claim 12 wherein the coating is absorbable by a body.

22. The surgical patch of claim 1 wherein the piece of material is absorbable by a body.

23. The surgical patch of claim 1 wherein the surgical fastener includes a suture.

24. The surgical patch of claim 1, wherein the surgical patch includes a first end approximately 1.97 inches long and a second end approximately 2.17 inches long.

25. The surgical patch of claim 24, wherein the surgical patch includes third and fourth ends approximately 1.78 inches long.

26. The surgical patch of claim 1 wherein the apertures are approximately 0.17 inches in diameter.

27. The surgical patch of claim 1 wherein the apertures are spaced approximately 0.4 inches apart.

28. The surgical patch of claim 1, wherein the surgical patch applies a force sufficient to treat herniated tissue.

29. The surgical patch of claim 28, wherein the herniated tissue is a cystocele.

30. The surgical patch of claim 28, wherein the herniated tissue is a rectocele.

31. The surgical patch of claim 28, wherein the herniated tissue is a enterocele.

32. The surgical patch of claim 28, wherein the surgical fastener includes a bone anchor.

33. The surgical patch of claim 29, wherein the stable anatomical structure includes bone.

* * * * *

UNITED STATES PATENT AND TRADEMARK OFFICE
CERTIFICATE OF CORRECTION

PATENT NO. : 6,197,036 B1  
DATED : March 6, 2001  
INVENTOR(S) : Tripp et al.

Page 1 of 1

It is certified that error appears in the above-identified patent and that said Letters Patent is hereby corrected as shown below:

<u>Title page,</u>
Item [56], FOREIGN PATENT DOCUMENTS, insert
-- WO 96/06567    3/1996 (WO).
   WO 97/13465    4/1997 (WO). --

Item [54], Title, delete "PELVIC FLOOR RECONSTRUCTION" and replace with the Title -- SURGICAL PATCH --.

Signed and Sealed this

Twenty-second Day of January, 2002

Attest:

JAMES E. ROGAN
*Attesting Officer*    *Director of the United States Patent and Trademark Office*